US00PP12538P2

(12) United States Plant Patent
Heims

(10) Patent No.: US PP12,538 P2
(45) Date of Patent: Apr. 9, 2002

(54) PULMONARIA PLANT NAMED 'RASPBERRY ICE'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/628,368

(22) Filed: Jul. 31, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct hybrid of Pulmonaria plant characterized by a unique combination of white margins and a frosted, mottled appearance.

1 Drawing Sheet

The present invention relates to a new and distinct Pulmonaria, of the family Boraginaceae, which originated as a tissue culture mutation of a Pulmonaria named 'Raspberry Splash' (U.S. Plant Pat. No. 12,138). Due to the fact that the 'Raspberry Splash' and its parent plants are the result of crosses between several different Pulmonaria species, no species designations are given.

This new Pulmonaria is a result of careful screening for tissue culture sports. The new variety has been reproduced only by asexual propagation (division and tissue culture). Each of the progeny exhibits identical characteristics to the original plant.

This plant is characterized by the following:

1. White-edged variegation on lance shaped leaves.
2. Silver mottling of leaves with silvery overlay of the green, central leaf area.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Pulmonaria 'Raspberry Ice' in Canby, Oreg.

DETAILED PLANT DESCRIPTION

The following is a detailed description of the new Pulmonaria hybrid based on observations of one and a half year old specimens in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—55 cm wide and 30 cm tall.
- *Form.*—Basal clump.

Foliage:
- *Type.*—Simple.
- *Shape.*—Lanceolate.

- *Length.*—13 to 20 cm.
- *Width.*—3 to 6 cm.
- *Petiole length.*—2 to 15 cm.
- *Margins.*—Entire, ciliate, irregularly undulating.
- *Apex.*—Narrowly acute.
- *Base.*—Attenuate.
- *Leaf texture.*—Setose. Irregularly rugose.
- *Petiole texture.*—Setose.
- *Leaf arrangement.*—Rosette.
- *Venation.*—Reticulate-pinnate.

Flower:
- *Type.*—Complete. Perfect.
- *Shape.*—Campanulate.
- *Size.*—4 to 5 mm from petal tip to petal tip.
- *Corolla.*—5 fused petals.
- *Corolla texture.*—Satiny.
- *Calyx.*—5 fused sepals.
- *Calyx size.*—1 cm deep and 0.7 cm wide.
- *Calyx texture.*—Setose.
- *Ovary position.*—Partly inferior.
- *Carpel number.*—4.
- *Pistil.*—Pin type, exerted from the corolla tube.
- *Stamen number.*—5.
- *Anthers.*—Attached to corolla tube.
- *Inflorescence type.*—Forked cymes.
- *Flower number per inflorescence.*—15 to 35 with 5 to 10 open at a given time.
- *Peduncle height.*—17 to 20 cm.
- *Peduncle width.*—3 mm tapering to 1.5 mm at apex.
- *Peduncle texture.*—Setose.
- *Bloom period.*—Early April to mid-June.
- *Fragrance.*—None.
- *Lastingness (inflorescence).*—7 days on the plant if not pollinated, 2–4 days off the plant or if pollinated.

Seed:
- *Type.*—4 smooth nutlets, dark brown.
- *Size.*—0.4 cm. long.
- *Shape.*—Ovoid.
- *Fertility.*—Seed is formed but is not fertile.

Disease: Susceptible to powdery mildew as are most Pulmonaria.

Color Characteristics

Foliage:

*Upper surface, margin.*—RHS 155C White Group.

*Upper surface.*—Close to RHS 191A Greyed-Green Group but darker. Occasional patches or streaks of RHS 139A Green Group may be seen.

*Upper surface, mottled area.*—RHS 190A Greyed-Green Group.

*Lower surface.*—RHS 191A–B Greyed-Green Group.

Flower:

*Bud.*—RHS 58A.

*Corolla.*—RHS 58A on young flower and 63B Red-Purple Group on mature.

*Pollen.*—RHS 155B White Group.

*Calyx.*—RHS 2D Yellow Group.

Peduncle: RHS 143C–D Green Group.

Seed: RHS 200A Brown Group.

DESCRIPTION OF PARENT PLANTS

The instant plant resulted from a sport of Pulmonaria 'Raspberry Splash' (U.S. Plant Pat. No. 12,138). Pulmonaria 'Raspberry Splash' has lance-shaped, well-marked, dark green foliage and large bright raspberry-colored flowers. Pulmonaria 'Raspberry Ice' differs in having a white margin, a frosted, mottled appearance, and smaller flowers.

Compared to *Pulmonaria rubra* 'David Ward', an unpatented plant, Pulmonaria 'Raspberry Ice' has narrower leaves of a gray green color rather than yellow green, more mottling on the leaves, and raspberry rather than salmon colored flowers.

I claim:

1. A new and distinct hybrid of Pulmonaria plant substantially as shown and described, characterized by a unique combination of white margins and a frosted, mottled appearance.

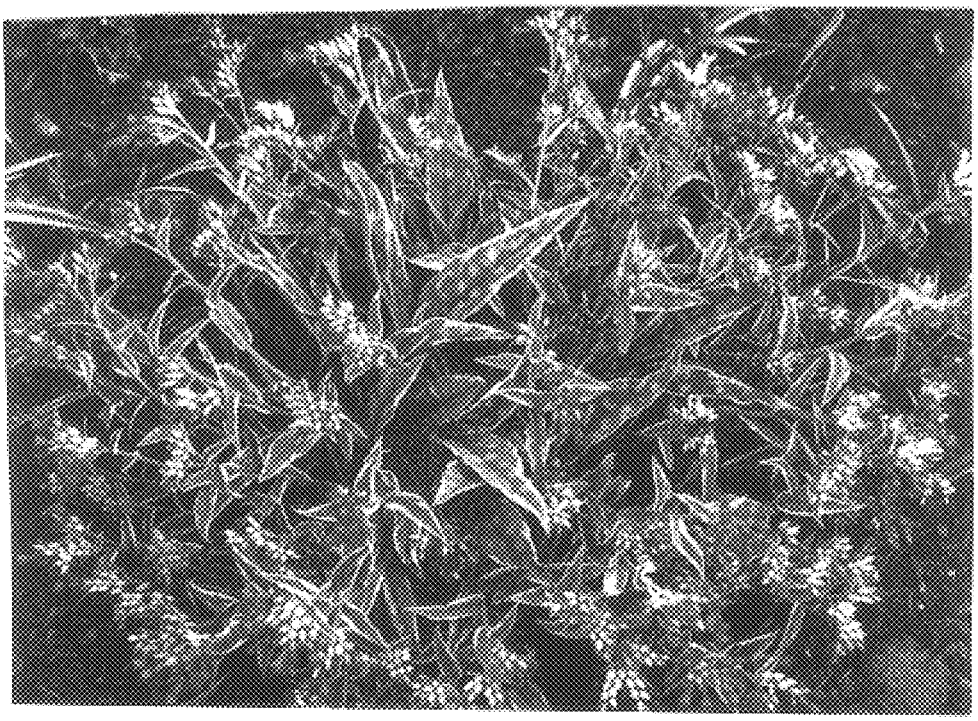

* * * * *